United States Patent
Cardin et al.

(10) Patent No.: US 9,668,709 B2
(45) Date of Patent: Jun. 6, 2017

(54) BARRIER ENVELOPE FOR AN IMAGING PLATE

(71) Applicant: The Tapemark Company, West St. Paul, MN (US)

(72) Inventors: Julie A. Cardin, Hastings, MN (US); Patricia Kitchen, Park City, UT (US); Steven A. Rau, Farmington, MN (US)

(73) Assignee: The Tapemark Company, West St. Paul, MN (US)

( * ) Notice: Subject to any disclaimer, the term of this patent is extended or adjusted under 35 U.S.C. 154(b) by 87 days.

(21) Appl. No.: 14/685,237

(22) Filed: Apr. 13, 2015

(65) Prior Publication Data

US 2015/0289830 A1    Oct. 15, 2015

Related U.S. Application Data

(60) Provisional application No. 61/978,439, filed on Apr. 11, 2014.

(51) Int. Cl.
*A61B 6/14* (2006.01)
*A61B 6/00* (2006.01)

(52) U.S. Cl.
CPC ............ *A61B 6/4423* (2013.01); *A61B 6/145* (2013.01); *A61B 6/425* (2013.01)

(58) Field of Classification Search
CPC ........ A61B 6/4423; A61B 6/145; A61B 6/425
See application file for complete search history.

(56) References Cited

U.S. PATENT DOCUMENTS

| | | |
|---|---|---|
| 1,293,323 A | 2/1919 | Buck |
| 1,370,858 A | 4/1921 | Tousey |
| 1,394,503 A | 10/1921 | Taylor |
| 1,437,827 A | 12/1922 | Sulzer et al. |
| 1,536,345 A | 5/1925 | Jones et al. |
| 1,537,925 A | 5/1925 | Bolin |
| 1,631,497 A | 6/1927 | Marler |

(Continued)

FOREIGN PATENT DOCUMENTS

| | | |
|---|---|---|
| EP | 0249878 | 12/1987 |
| EP | 0363092 | 4/1990 |

(Continued)

OTHER PUBLICATIONS

"Deluxe Safe 'n' Sure Envelopes by Flow Dental," http://www.flowdental.com/main.php?page=products&cat=17&, 2 pages.

(Continued)

*Primary Examiner* — Wyatt Stoffa
*Assistant Examiner* — Eliza Osenbaugh-Stewar
(74) *Attorney, Agent, or Firm* — Pauly, DeVries Smith & Deffner, LLC (57) ABSTRACT

Examples include an envelope for an imaging plate. The envelope can include an opaque film partially hermetically sealed with a transparent film defining a cavity between the opaque film and the transparent film; the cavity configured to receive an imaging plate; an adhesive disposed on the opaque film or the transparent film along an unsealed portion of the opaque film and the transparent film; and a notch defined by the opaque film and the transparent film along a tab portion of the opaque film and transparent film that is hermetically sealed.

20 Claims, 7 Drawing Sheets

(56) References Cited

U.S. PATENT DOCUMENTS

| | | |
|---|---|---|
| 1,738,467 A | 12/1929 | Warren |
| 1,994,579 A | 4/1935 | Hodgson |
| 2,071,110 A | 2/1937 | Burke |
| 2,084,092 A | 6/1937 | Kenney |
| 3,189,174 A | 6/1965 | Cormack |
| 3,551,673 A | 12/1970 | Siegel |
| 4,238,541 A | 12/1980 | Burton et al. |
| 4,251,732 A | 2/1981 | Fried et al. |
| 4,791,657 A | 12/1988 | Kirsch et al. |
| 4,831,643 A | 5/1989 | Tanaka et al. |
| 4,834,241 A | 5/1989 | Southern et al. |
| 4,834,245 A | 5/1989 | Ohga et al. |
| 4,912,740 A | 3/1990 | Liese, Jr. et al. |
| 4,937,040 A | 6/1990 | Holcomb et al. |
| 5,044,008 A | 8/1991 | Jackson et al. |
| 5,239,805 A | 8/1993 | Imai et al. |
| 5,251,755 A | 10/1993 | Kausch et al. |
| 5,285,491 A | 2/1994 | Muylle et al. |
| 5,450,710 A | 9/1995 | Jensen et al. |
| 5,466,561 A | 11/1995 | Rantanen |
| 5,477,310 A | 12/1995 | Lamb et al. |
| 5,613,779 A | 3/1997 | Niwa |
| 5,765,342 A | 6/1998 | Jensen et al. |
| 5,997,111 A | 12/1999 | Jensen et al. |
| 6,216,870 B1 | 4/2001 | Welp et al. |
| 6,468,611 B1 | 10/2002 | Haskin et al. |
| 6,827,214 B2 * | 12/2004 | Alzner .................. G03C 3/003 206/455 |
| 6,866,149 B2 | 3/2005 | Alzner |
| 7,320,204 B2 | 1/2008 | Alzner et al. |
| 7,599,679 B2 | 10/2009 | Awiszus |
| 7,794,143 B2 | 9/2010 | Allmer et al. |
| 8,005,455 B2 | 8/2011 | Awiszus |
| 8,271,340 B2 | 9/2012 | Awiszus |
| 2004/0169149 A1 | 9/2004 | Alzner et al. |
| 2005/0051738 A1 | 3/2005 | Alzner et al. |
| 2005/0232575 A1 * | 10/2005 | Koren ..................... A61B 6/00 386/361 |
| 2007/0001133 A1 | 1/2007 | Alzner et al. |
| 2007/0072774 A1 | 3/2007 | Mori et al. |
| 2008/0017539 A1 | 1/2008 | Alzner et al. |
| 2010/0098220 A1 | 4/2010 | Allmer et al. |
| 2011/0237994 A1 * | 9/2011 | Russ ................. A61F 13/00034 602/46 |

FOREIGN PATENT DOCUMENTS

| | | |
|---|---|---|
| EP | 1136878 | 10/2005 |
| JP | 2003072773 | 3/2003 |

OTHER PUBLICATIONS

"Econo Safe 'n' Sure Phosphor Plate Envelopes with Thumb Notch," http://www.flowdental.com/main.php?page=products&cat=17&, 2 pages.

"Plasdent Barrier Envelope," https://www.pattersondental.com/Supplies/ProductFamilyDetails/13746, 1 page.

* cited by examiner

BARRIER ENVELOPE FOR AN IMAGING PLATE

CLAIM OF PRIORITY

This application claims the benefit of U.S. Provisional Application No. 61/978,439, filed Apr. 11, 2014, the content of which is herein incorporated by reference in its entirety.

FIELD

Examples described herein relate to a barrier envelope. More specifically, the examples herein relate to a barrier envelope for reusable imaging plates.

BACKGROUND

Reusable imaging plates are frequently used in dentistry as opposed to traditional x-ray film for digital imaging systems. An imaging plate can be inserted into a barrier envelope and then inserted into the desired position within the patient's oral cavity.

The envelope can help protect the imaging plate from contamination, such as from the patient's saliva. The imaging plate can be removed from the envelope and inserted into a new envelope for further use, such as with a different patient. The first envelope can be discarded after use.

The user, such as a dentist, oral hygienist, or technician, can be wearing gloves or other personal protective equipment that can make handling the envelope and imaging plate difficult. Accordingly, there is a need for an envelope that can be more easily handled by a user.

SUMMARY

Embodiments included herein include an envelope for an imaging plate. The envelope can include a first film partially hermetically sealed with a second film in a sealed portion, the first film and second film defining a cavity between the first film and the second film, the cavity configured to receive an imaging plate; an adhesive disposed on the first film or the second film along an unsealed portion of the first film and the second film; a tab portion protruding from a remainder of the envelope; and a recess defined by the first film and the second film within the tab portion and within the sealed portion.

In an embodiment, the sealed portion of the first film and the second film is around a portion of a periphery of the envelope.

In an embodiment, the envelope can further include a non-woven peel strip covering at least a portion of the adhesive.

In an embodiment, the recess is a Z-shaped recess.

In an embodiment, the envelope can further include a slit passing through both the first and second films.

In an embodiment, the slit is separated from the recess by a portion of the first film and the second film.

In an embodiment, the recess is at least partially defined by a zig-zag side.

In an embodiment, an envelope can include an first film partially hermetically sealed with a second film in a sealed portion, the first film and second film defining a cavity between the first film and the second film, the cavity configured to receive an imaging plate; an adhesive disposed on the first film or the second film along an unsealed portion of the first film and the second film; a recess defined by the first film and the second film within the sealed portion; and a slit defined by the first film or the second film separated from the recess.

In an embodiment, the sealed portion is around a portion of a periphery of the envelope.

In an embodiment, the envelope has four sides, wherein the sealed portion is along three sides, and wherein the adhesive is present along a remaining side.

In an embodiment, the envelope can further include a tab portion protruding from a remainder of the envelope.

In an embodiment, the tab defines the recess.

In an embodiment, the slit is parallel with an edge of the envelope that is within the unsealed portion.

In an embodiment, the slit extends through both the second and first films.

In an embodiment, the slit extends normal to the recess.

In an embodiment, the recess is at least partially defined by a zig-zag side.

In an embodiment, the envelope can further include a tear line along one of the first film or the second film, wherein the tear line includes at least one weaker portion of the first film or the second film.

In an embodiment, the tear line extends from a portion of the recess in a direction to be approximately parallel to a top edge or bottom edge of the envelope.

In an embodiment, the tear line extends from a portion of the recess toward a side of the envelope that is opposite from the recess.

In an embodiment, the first film comprises an opaque film and the second film comprises a transparent film.

In an embodiment, the envelope can include an opaque film partially hermetically sealed with a transparent film in a sealed portion, the opaque film and transparent film defining a cavity between the opaque film and the transparent film, the cavity configured to receive an imaging plate; an adhesive disposed on the opaque film or the transparent film along an unsealed portion of the opaque film and the transparent film; a tab portion protruding from a remainder of the envelope, the tab portion being within the sealed portion; a recess defined by the opaque film and the transparent film within the sealed portion and within the tab portion; a tear line along one of the opaque film or the transparent film, wherein the tear line includes a series of weakened portions of the opaque film or the transparent film; and a slit defined by at least one of the opaque film or the transparent film, and separated from the recess by at least a portion of the opaque film and the transparent film.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The examples herein may be more completely understood in connection with the following drawings, in which.

While the invention is susceptible to various modifications and alternative forms, specifics thereof have been shown by way of example and drawings, and will be described in detail. It should be understood, however, that the invention is not limited to the particular examples described. On the contrary, the intention is to cover modifications, equivalents, and alternatives falling within the spirit and scope of the invention.

DETAILED DESCRIPTION

The examples of the present invention described herein are not intended to be exhaustive or to limit the invention to the precise forms disclosed in the following detailed description. Rather, the examples are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Figures 1, 3:
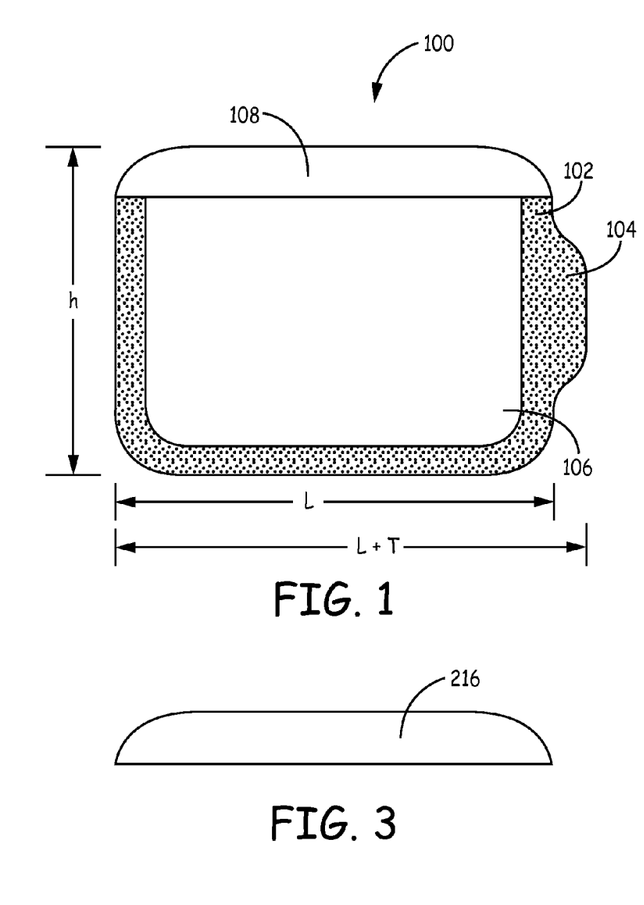
FIG. 1 is a front view of an envelope, according to an example.
FIG. 3 is a front view of a peel strip, according to an example.

In reference now to the figures, FIG. 1 shows a front view of an envelope 100, according to an example. In an example, the envelope 100 can include a first film and a second film. The first film can include an opaque film, such as a film that allows little to no light to pass through. The second film can include a transparent film or a translucent film, such as a film that allows light to pass through or penetrate the film. In another example, the first film is transparent while the second film is opaque. In another example, both the first and second films can be opaque. In another example, both the first and second films can be transparent.

In an example, the first film can be coupled to the second film, such as by heat sealing the two films together. The first film can be coupled to the second film along a seal area or sealed portion 102, such as a portion of the first film that is sealed together with the second film. The seal can be a destructive seal, such that to separate the first film from the second film at the seal area would destroy at least a portion of the first film or the second film. The seal can be formed by heat sealing, ultrasonic sealing, adhesive or other sealing techniques.

One or more of the edges of the first or second film can include a tab portion 104. The tab portion 104 protrudes from a remainder of the envelope. In an example, the tab portion 104 is located in the middle of the envelope, such as equally between the top edge of the envelope 100 and the bottom edge of the envelope 100. In an example, the tab portion 104 is located along the edge of the envelope 100, such as a side edge of the envelope 100 (as shown in FIG. 1). The tab portion 104 can extend along a portion of the perimeter of the envelope 100. The tab portion 104 can be a bump out along the perimeter of the envelope 100. The tab portion 104 can be located within the seal area 102. The tab portion 104 can be in the same plane as the first film and the second film. The tab portion 104 can include a portion of the first film and a portion of the second film. The tab portion 104 can extend along a majority of one side of the envelope. The tab portion can extend along 75% or more of one side of the envelope.

In an example, coupling the first film with the second film can define a cavity 106, such as an area between the first film and second film that is not sealed. In an example, the seal area 102 can define at least a portion of the perimeter of the cavity 106. In an example, the envelope defines a generally rectangular shape with four major sides. In an example, the seal area 102 extends along three of those major sides. An imaging plate can be inserted within the envelope 100, such as within the cavity 106.

In an example, the envelope 100 can include a cavity opening 108, such as a portion of the periphery of the cavity 106 that is not included within the seal area 102. The cavity opening 108 can be along an edge of the envelope 100. The cavity opening 108 can be unsealed in a first state and sealed in a second state. The first state can be representative of before a user inserts an imaging plate into the cavity 106. After the user inserts an imaging plate into the cavity 106, the user can remove a peel strip exposing an adhesive (shown in FIG. 2). The adhesive can couple or seal the first film to the second film along the cavity opening 108, such as to enclose the imaging plate within the cavity 106.

In an example, the envelope 100 can have a height (h) of at least 1.10 inches and no more than 1.75 inches. In an example, the envelope 100 can have a height of at least 1.26 inches and no more than 1.62 inches. In an example, the envelope 100 can have a length of at least 1.50 inches and no more than 2.10 inches. In an example, the envelope 100 can have a length of at least 1.69 inches and no more than 1.99 inches. In an example, the envelope 100 can have a length with the tab portion 104 of at least 1.60 inches and no more than 2.25 inches. In an example, the envelope 100 can have a length with the tab portion 104 of at least 1.81 inches and no more than 2.11 inches.

In an example, the envelope 100 can have a height (h) of at least 1.10 inches. In an example, the envelope 100 can have a height of no more than 1.75 inches. In an example, the envelope 100 can have a height of at least 1.26 inches. In an example, the envelope 100 can have a height of no more than 1.62 inches.

In an example, the envelope 100 can have a length (L) of at least 1.50 inches. In an example, the envelope 100 can have a length of no more than 2.10 inches. In an example, the envelope 100 can have a length of at least 1.69 inches. In an example, the envelope 100 can have a length of no more than 1.99 inches.

In an example, the envelope 100 can have a length with the tab portion 104 (L+T) of at least 1.60 inches. In an example, the envelope 100 can have a length with the tab portion 104 of no more than 2.25 inches. In an example, the envelope 100 can have a length with the tab portion 104 of at least 1.81 inches. In an example, the envelope 100 can have a length with the tab portion 104 of no more than 2.11 inches.

In an example, the envelope 100 can have a length with the tab portion 104 (L+T) of at least 4.064 centimeters. In an example, the envelope 100 can have a length with the tab portion 104 of no more than 5.715 centimeters. In an example, the envelope 100 can have a length with the tab portion 104 of at least 4.597 centimeters. In an example, the envelope 100 can have a length with the tab portion 104 of no more than 5.359 centimeters.

Figure 2:
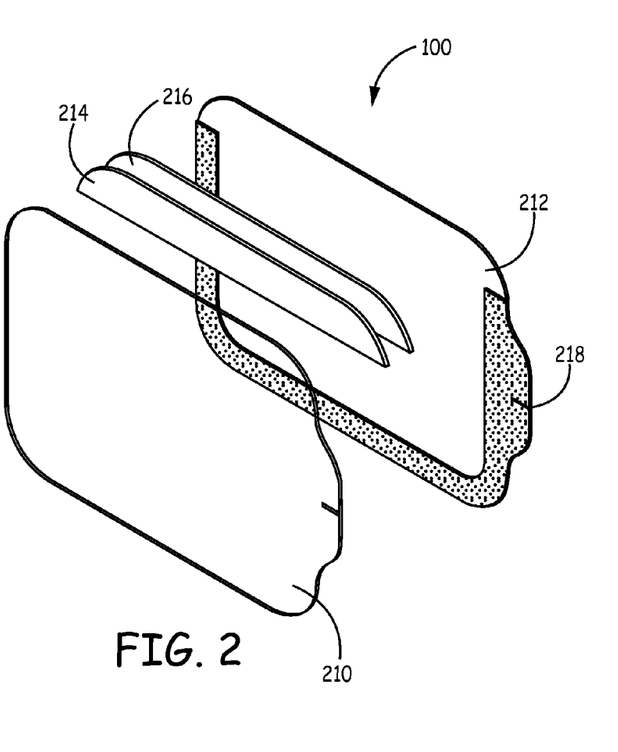
FIG. 2 is an exploded view of an envelope, according to an example.

FIG. 2 shows an exploded view of an envelope 100, according to an example. The envelope 100 can include a first film 210 and a second film 212. In an example, adhesive 214 is disposed on the first film 210. A peel strip 216 can be disposed on the adhesive 214. The peel strip 216 can easily be removed from the adhesive 214, such as by the user pulling the peel strip 216 in a direction away from the adhesive 214 and the first film 210. In an alternative example, the adhesive 214 can be disposed on the second film 212.

The adhesive 214 and the peel strip 216 can be disposed between the first film 210 and the second film 212, such that, when desired, the adhesive 214 can be exposed to couple the first film 210 with the second film 212. The peel strip 216 can protect the adhesive 214, such as by covering at least a portion of the adhesive 214 when the cavity opening 108 is to remain open. The peel strip 216 can protect the adhesive 214, such that the adhesive 214 cannot contact the second film 212. If the adhesive 214 does not contact the second film 212, the cavity opening 108 can remain open. The cavity opening 108 can remain open until an imaging plate is inserted into the cavity 106. The peel strip 216 can be removed from the adhesive 214, such as when an imaging plate has been inserted into the cavity 106. After the peel strip 216 has been removed, the cavity opening 108 can be sealed shut. The cavity opening 108 can be sealed shut by coupling the first film 210 with the second film 212, such as with the adhesive 214.

The envelope 100 can define a notch 218, such as a slit through the first film 210 and the second film 212. The notch 218 can define a point at which a user can start a tear, such as to tear the envelope 100 apart. The user can tear the envelope 100 apart, such as to gain access to the cavity 106, such as to remove the imaging plate from the envelope 100.

FIG. 3 is a front view of a peel strip 216, according to an example. The peel strip 216 can have a similar shape as a portion of the first film 210 or the second film 212. The peel strip 216 can have a linear edge, such as the edge that matches up with a bottom edge of the adhesive 214. The peel strip 216 can include symbols or letters, such as direction for the user on how to remove the peel strip 216 from the adhesive 214. The peel strip 216 can be non-woven.

Figure 4:
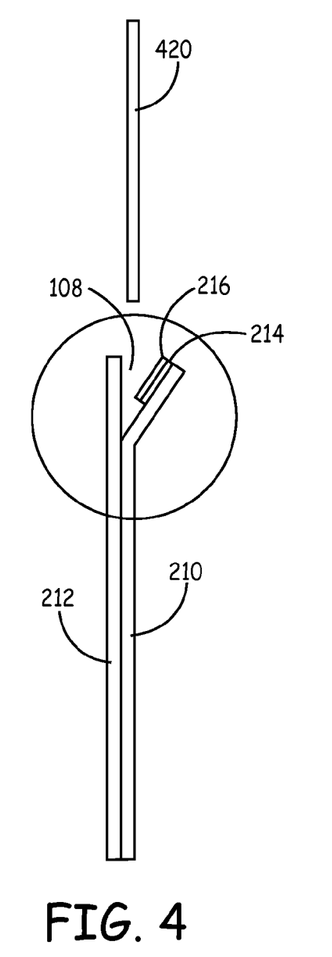
FIG. 4 is a side view of an envelope, according to an example.
Figure 5:
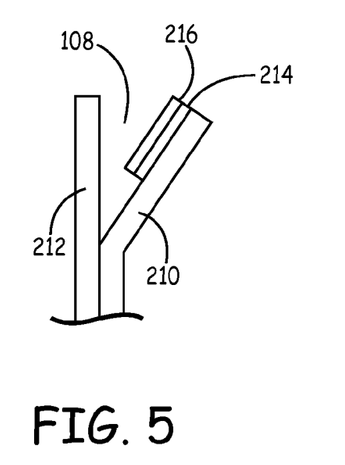
FIG. 5 is a close up view of the envelope shown in FIG. 4, according to an example.

FIG. 4 shows a side view of an envelope 100, according to an example. FIG. 5 shows a close up view of a portion of FIG. 4. As can be seen in FIG. 4, the first film 210 can be next to or adjacent to the second film 212. The first film 210 can be flexible, such that a top portion of the first film 210 can flex away from the second film 212. The first film 210 can flex away from the second film 212, such as at the cavity opening 108. The first film 210 can flex away from the second film 212, such as to allow the imaging plate 420 to be placed into a cavity defined between the first and second films. Similarly, the second film 212 can be flexible, such as to flex away from the first film 210. In an example, both the first film 210 and the second film 212 can be flexible.

After the imaging plate 420 is inserted into the envelope 100, the peel strip 216 can be removed and the adhesive 214 can be exposed. Once the adhesive 214 is exposed, the portion of the first film 210 that is flexed away from the second film 212 can be unflexed, such that the adhesive 214 comes in contact with the second film 212. The adhesive 214 can couple a portion of the first film 210 with a portion of the second film 212, such as to close the cavity opening 108, and seal the imaging plate 420 inside the cavity 106. The adhesive 214 can create a destructive seal between the first film 210 and the second film 212, such that if the first film 210 is attempted to be separated from the second film 212 at a seal area, at least a portion of the first film 210 or the second film 212 will be destroyed.

Figure 6:
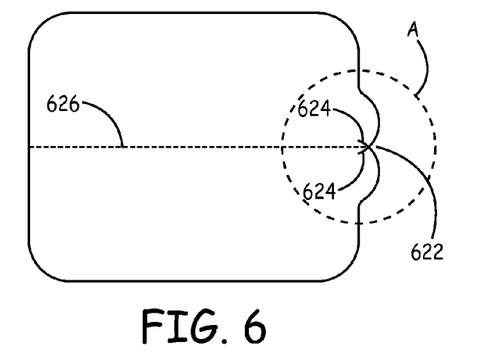
FIG. 6 is a front view of an envelope, according to an example.
Figure 7:
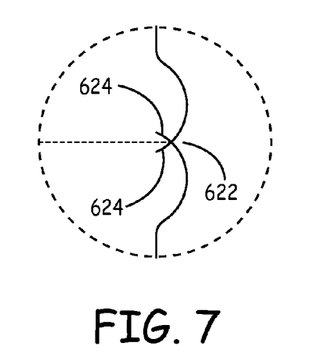
FIG. 7 is a close up of a portion of FIG. 6, according to an example.

FIGS. 6-16 show different examples of a notch. As shown in FIG. 6, in some examples, the notch 218 can include a recess 622 and a slit 624. FIG. 7 shows a close up view of portion A in FIG. 6. The envelope 100 can define the recess 622, such as a "U" shaped recess along a side of the envelope 100. In an example, the first film 210 and the second film 212 define the recess 622. In an example, only one of the first film 210 or the second film 212 can define the recess 622.

The recess 622 can define a point at which the user can start to tear or otherwise separate the envelope 100 to gain access to the cavity 106, such as to remove the imaging plate 420. The recess 622 can be a void of material or film at a portion of the envelope 100. The recess 622 can extend in from the perimeter of the envelope 100 towards the cavity 106. The recess 622 can terminate before the cavity 106, such that there is at least some seal area 102 between the recess 622 and the cavity 106. The recess 622 can include nonlinear edges, such as shown in FIG. 6.

The notch 218 can also include a slit 624. The slit 624 can be a cut in the envelope 100 or a separation in the envelope 100. The slit 624 can extend from the recess 624, such as towards the cavity 106. The slit 624 can terminate prior to the cavity 106, such that at least a portion of the seal area 102 is located between the slit 624 and the cavity 106. Further, the slit 624 can be perpendicular to the edge of the envelope 100, such that the slit 624 is aligned with the grains in the film. In an example, such as shown in FIG. 6, the envelope 100 can define more than one slit 624. The slit 624 can be nonlinear, such as an arc.

The first film 210 and the second film 212 can include a polymer. The polymer can include grains. The grains in the polymer can be substantially aligned in a similar direction. In an example, it can take less force to tear the envelope in a direction parallel with the grain than in a direction perpendicular to the grain. In an example, the tear line 626 or slit 624 can be aligned or parallel with the grain, such that it is easier for the user to tear the envelope 100.

Figure 24:
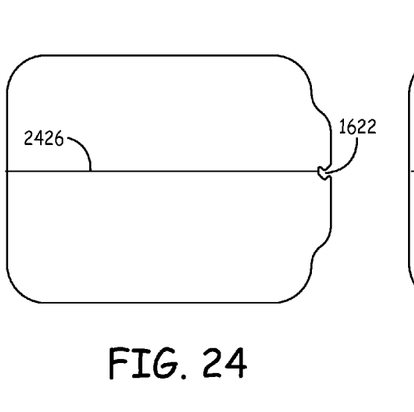
FIG. 24 is a front view of an envelope, according to an example.

The envelope 100 can include a tear line 626. The tear line 626 can be a portion of the envelope that is weakened, such that it is easier to tear the envelope 100 apart. The tear line 626 can include a perforation. In an example, the tear line 626 can be stamped. In an example, the tear line 626 can be pressed. The tear line 626 can be a plurality of weakened segments, such as segments of the first film 210 or the second film 212 that are thinner than the portions of the first film 210 or the second film 212 that are not part of the tear line 626. In an example, the tear line can include a continuous weakened portion, such as shown in FIG. 24.

In an example, the tear line 626 can extend from one edge of the envelope 100 to an area near the end of the slit 624. In an example, the tear line 626 can start from the end of the slit 624. In an example, the tear line 626 can be lined up with the termination point of the slit 624. In an example, the tear line 626 can be offset from the slit 624. In an example, the tear line 626 can extend from the slit 624 to the opposite edge of the envelope 100. In an example, the tear line 626 can extend from one edge of the envelope 100 to the other edge of the envelope 100.

In an example, the first film 210 includes a tear line 626. In an example, the second film 212 includes a tear line 626. In an example, both the first film 210 and the second film 212 include a tear line 626. In an example the tear line 626 can be added to the first film 210 or the second film 212 prior to sealing the first film 210 with the second film 212. The tear line 626 can extend across the first film 210 or the second film 212, such as from one edge to an opposite edge. In an example, at least a portion of the tear line 626 can be included in the seal area 102, when the first film 210 is sealed with the second film 212, such as to create the seal zone 102.

In an example the first film 210 can be weakened along a tear line 626, such that less force is needed to tear the envelope 100. In an example, the second film 212 can be weakened along a tear line 626, such that less force is needed to tear the envelope 100. In an example, both the first film 210 and the second film 212 can be weakened along a tear line 626. In an example where the envelope 100 includes a tear line 626, the cavity 106 can still be isolated, such that cavity can be hermetically sealed or sealed, such that no exterior elements, such as air or liquid, can enter the cavity 106 after the cavity 106 has been sealed and before the envelope 100 has been torn apart.

The cavity 106 can be hermetically sealed and withstand a range of pH. In an example, the envelope 100 can withstand a pH of at least 2 and no more than 12. In an example, the envelope 100 can withstand a pH of at least 3 and no more than 11. In an example, the envelope 100 can withstand a pH of at least 4 and no more than 10. In an example, the envelope 100 can withstand a pH of at least 5 and no more than 9. In an example, the envelope 100 can withstand a pH of at least 2. In an example, the envelope 100 can withstand a pH of at least 3 or higher. In an example, the envelope 100 can withstand a pH of at least 4 or higher. In an example, the envelope 100 can withstand a pH of at least 5 or higher. In an example, the envelope 100 can withstand a pH of 12 or lower. In an example, the envelope 100 can withstand a pH of 11 or lower. In an example, the envelope 100 can withstand a pH of 10 or lower. In an example, the envelope 100 can withstand a pH of 9 or lower. In an example, the envelope 100 can withstand a pH if the envelope 100 can remain hermetically sealed when the envelope 100 is in contact with a fluid of the given pH for at least two minutes.

As shown in FIG. 6, the notch 622 can be located on the tab portion 104. The notch 622 can be equally spaced from the top edge of the envelope 100 and the bottom edge of the envelope 100. In an example, the notch 622 is located in the middle of the tab portion 104. The recess 622 can be "V" shaped or "U" shaped. In an example, the tear line 626 can be located at a midpoint between two slits 624.

Figure 8:
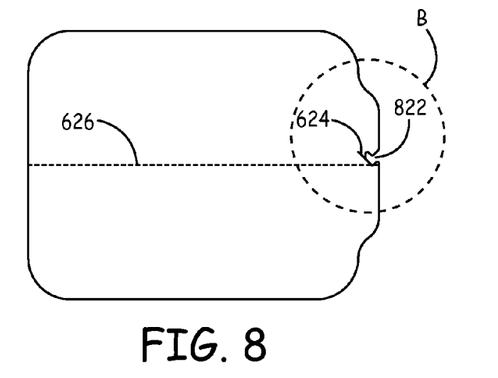
FIG. 8 is a front view of an envelope, according to an example.
Figure 9:
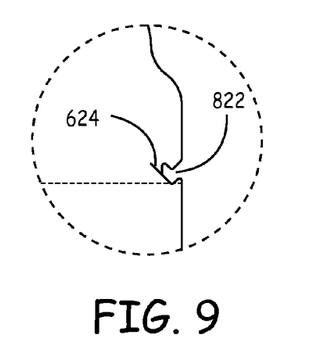
FIG. 9 is a close up of a portion of FIG. 8, according to an example.

FIG. 8 shows a front view of an envelope 100, according to an example. FIG. 9 shows a close up view of portion B in FIG. 8. The recess 822 can be "Z" shaped. One side of the recess 822 can include a zig-zag portion that changes direction, which results in a portion of material of the envelope protruding into the area of the recess 822. The portion of the recess 822 closest to the cavity 106 can be linear, such that the portion of the recess 822 closest to the cavity 106 is parallel with the edge of the cavity 106 or the edge of the envelope 100.

Figure 16:
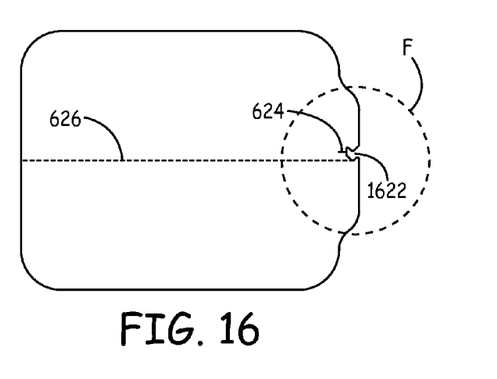
FIG. 16 is a front view of an envelope, according to an example.

The slit 624 can extend from the recess 106, such as the linear portion of the recess 822. The slit 624 can be perpendicular with the linear portion of the recess 822 (as shown in FIG. 16). Alternatively, the slit 624 can extend at a non-perpendicular angle from the linear portion, such as the slit 624 does not align with the grain in the first film 210 or second film 212 (as shown in FIG. 8).

In an example, the tear line 626 can extend from a portion of the recess 822. The tear line 626 can extend from the end of the slit 624.

Figure 10:
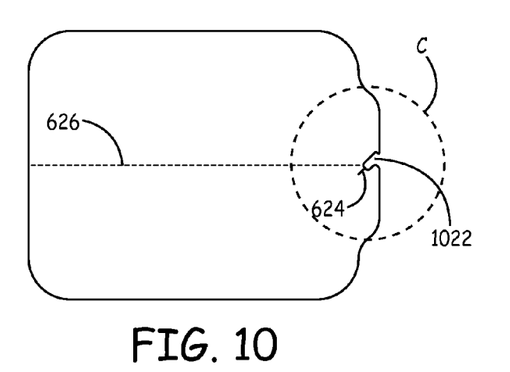
FIG. 10 is a front view of an envelope, according to an example.
Figure 11:
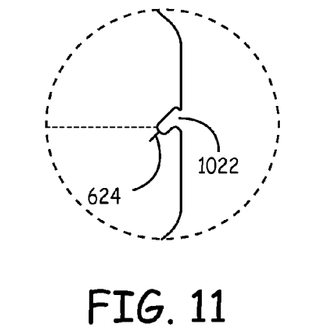
FIG. 11 is a close up of a portion of FIG. 10, according to an example.

FIG. 10 shows a front view of an envelope 100, according to an example. FIG. 11 shows a close up view of portion C in FIG. 10. The recess 1022 can be "U" shaped. The "U" shape can have a linear bottom edge. The "U" shape can be non-perpendicular from the edge of the envelope 100. The slit 624 can extend from the bottom of the "U" shape, such as the bottom linear portion of the "U" shape. The slit 624 can extend perpendicular to the bottom linear portion of the "U", such that the slit 624 is not perpendicular with the edge of the envelope 100.

Figure 12:
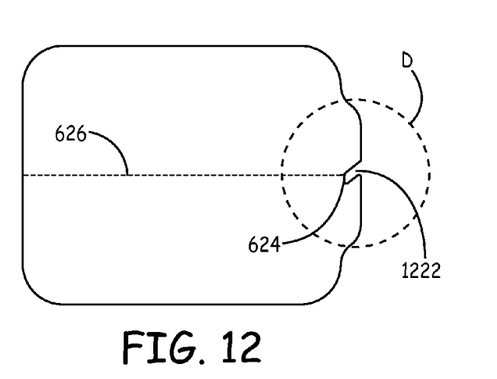
FIG. 12 is a front view of an envelope, according to an example.
Figure 13:
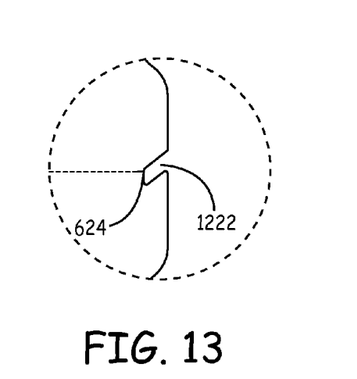
FIG. 13 is a close up of a portion of FIG. 12, according to an example.

FIG. 12 shows a front view of an envelope 100, according to an example. FIG. 13 shows a close up view of portion D in FIG. 12. The recess 1222 can be "U" shaped. The "U" shape can have a linear bottom edge. The linear bottom edge can be parallel with the edge of the envelope 100. The sides of the "U" can be non-perpendicular with the edge of the envelope 100. The slit 624 can extend from the bottom of the "U" shape, such as the bottom linear portion of the "U" shape. The slit 624 can extend perpendicular to the bottom linear portion of the "U", such that the slit 624 is perpendicular with the edge of the envelope 100.

Figure 14:
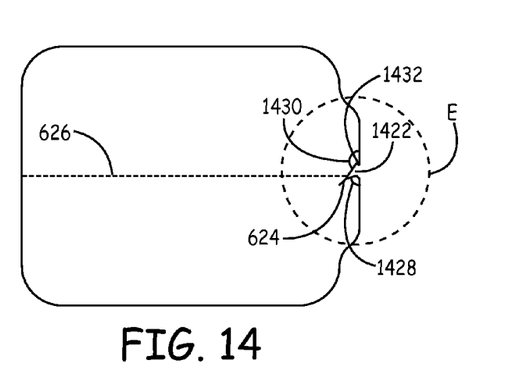
FIG. 14 is a front view of an envelope, according to an example.
Figure 15:
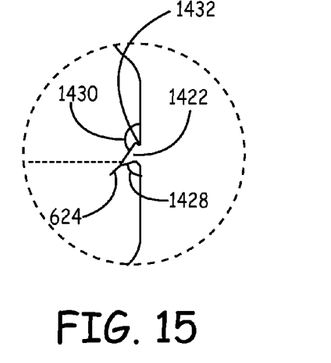
FIG. 15 is a close up of a portion of FIG. 14, according to an example.

FIG. 14 shows a front view of an envelope 100, according to an example. FIG. 15 shows a close up view of portion E in FIG. 14. The recess 1422 can be "V" shaped. The "V" shape can be offset from the edge of the envelop 100, such that the angle 1428 is not equal to angle 1430. Further, the "V" shape can have a discontinuity, such as the discontinuity 1432. The linear bottom edge can be parallel with the edge of the envelope 100. The sides of the "U" can be non-perpendicular with the edge of the envelope 100. The slit 624 can extend from the bottom of the "U" shape, such as the bottom linear portion of the "U" shape. The slit 624 can extend perpendicular to the bottom linear portion of the "U", such that the slit 624 is perpendicular with the edge of the envelope 100.

Figure 17:
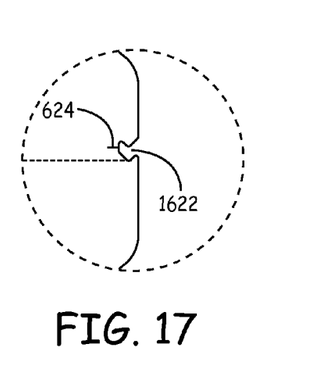
FIG. 17 is a close up of a portion of FIG. 16, according to an example.

FIG. 16 shows a front view of an envelope 100, according to an example. FIG. 17 shows a close up view of portion F in FIG. 16. The recess 1622 can be "Z" shaped, similar to FIG. 7. The portion of the recess 1622 closest to the cavity 106 can be linear, such that the portion of the recess 1622 closest to the cavity 106 is parallel with the edge of the cavity 106 or the edge of the envelope 100. The slit 624 can extend from the recess 106, such as the linear portion of the recess 1622. The slit 624 can be perpendicular with the linear portion of the recess 1622.

Figure 18:
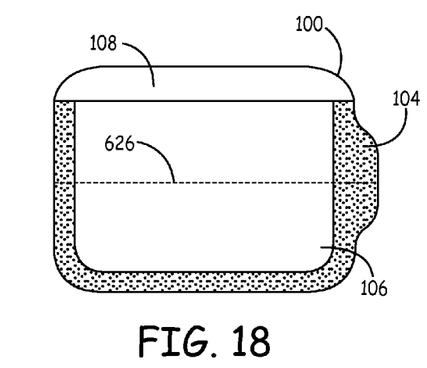
FIG. 18 is a front view of an envelope, according to an example.
Figure 19:
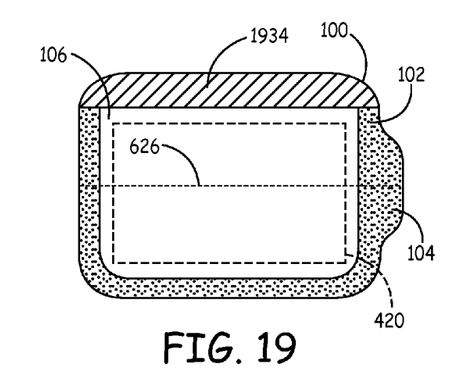
FIG. 19 is a front view of an envelope, according to an example.

FIGS. 18-22 show an envelope 100 in varies stages of use. FIG. 18 shows a front view of an envelope 100 prior to a user inserting an imaging plate into the envelope 100. FIG. 19 shows an envelope 100 with an imaging plate 420 disposed within the cavity 106. The cavity opening 108 can be closed after an imaging plate 420 is inserted into the envelop 100, such as with the adhesive 214. The peel strip 216 can be removed from the adhesive 214. The adhesive 214 can come in contact with the second film 212, such as to couple the first film 210 to the second film 212 and close the cavity opening 108. The adhesive seal area 1934 and the seal area 102 can enclose the cavity 106 with an imaging plate 420 disposed inside.

The envelope 100 and imaging plate 420 can be inserted into a patient's oral cavity, such as to capture the desired image. The envelope 100 and imaging plate 420 can be removed from the patient's oral cavity after the image is captured on the imaging plate 420.

Figure 20:
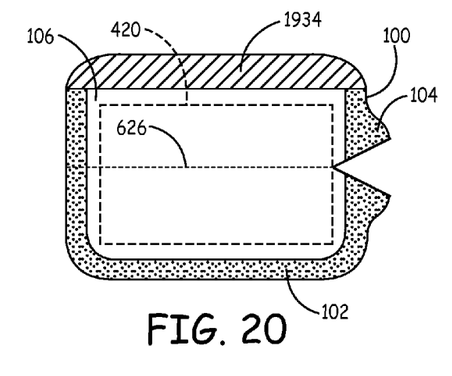
FIG. 20 is a front view of an envelope, according to an example.

The imaging plate 420 can be removed by opening the envelope 100, such as by tearing the envelope 100 along the tear line 626. FIG. 20 shows an envelope 100 partially torn along the tear line 616. In some instances, as a user tears the envelope 100 the separation created by the user might not line up with the tear line 626, such that the separation is above or below the tear line 626. The separation created by the user can start above or below the tear line 626 and then proceed to contact the tear line 626 as the separation continues across the envelope 100, such as if the separation is not parallel with the tear line 626 when the separation is above or below the tear line 626.

Figure 21:
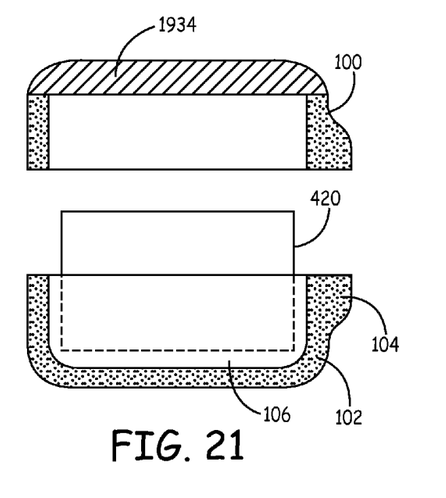
FIG. 21 is a front view of an envelope, according to an example.
Figure 22:
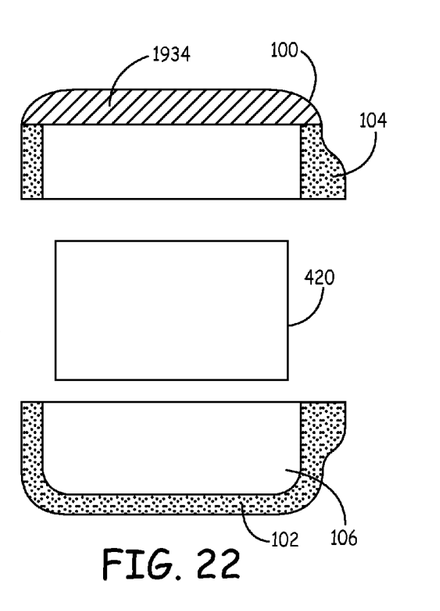
FIG. 22 is a front view of an envelope, according to an example.

After the envelope has been torn or otherwise opened, the imaging plate 420 can be removed from the cavity 106. The envelope 100 can then be discarded. FIG. 21 shows an envelope 100 that has been separated into two pieces, exposing the imaging plate 420. FIG. 22 shows an example of the envelope 100 after the imaging plate 420 has been removed from the cavity 106.

Figure 23A:
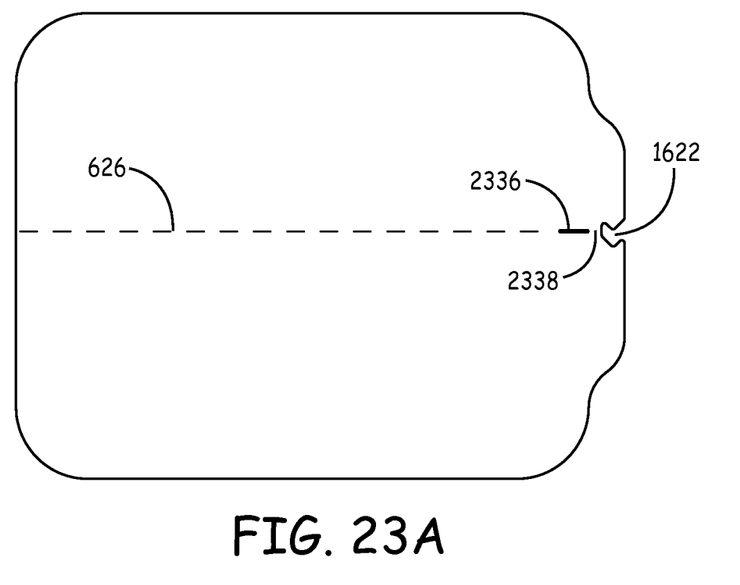
FIG. 23A is a front view of an envelope, according to an example.
Figure 23B:
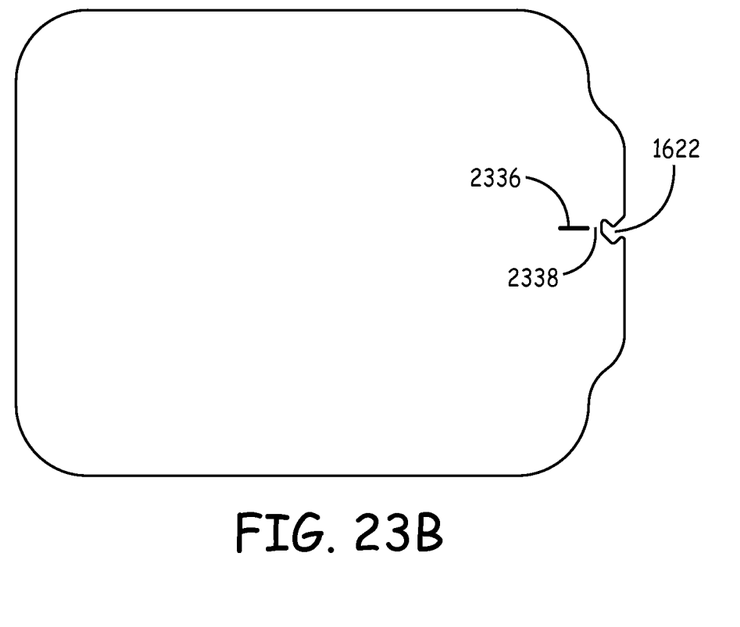
FIG. 23B is a front view of an envelope, according to an example.

FIG. 23A shows an envelope 100, according to an example. The envelope 100 can define a slit 2336, such as a void of material that extends through one or both of the films, or a weakened portion of material. In an example, the slit 2336 can include an aperture. In an example, the slit 2336 can be rectangular shaped, such as if the slit 2336 is formed by cutting the slit into the envelope 100, such as with a die. In an example, the slit 2336 can be separated from the recess 1622, such as by material 2338 extending between the recess 1622 and the slit 2336. The material 2338 can include a portion of at least one of the first film 210 or the second film 220 that extends between the recess 1622 and the slit 2336. In an example, a tear line 626 can extend from the end of the slit 2336, such as shown in FIG. 23A. FIG. 23B shows an envelope 100, according to an example. The envelope 100 can include a slit 2336 and not include a tear line.

In an example, the tear line can extend from the end of the recess. FIG. 24 shows a tear line 2426 extending from a portion of recess 1622 across the envelope 100. The tear line 2426, as discussed above, can include a series of weakened segments. In an example, the tear line 2426 can include a single weakened segment. The single weakened segment can extend from a recess or a slit across the envelope 100, such as shown in FIG. 24.

Figure 25:
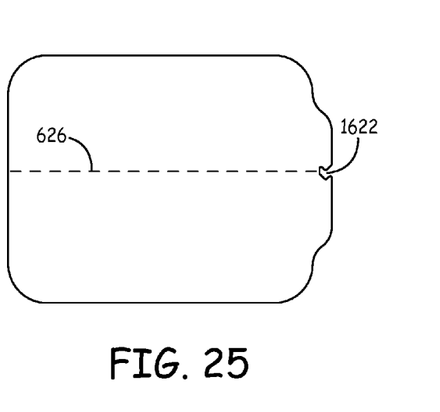
FIG. 25 is a front view of an envelope, according to an example.

In an example, the tear line 626 can extend from the recess 1622 (as shown in FIG. 25). An end of the tear line 626 can extend from the recess 1622 and across the envelope 100. In an example, the recess 1622 can be "Z" shaped or have zig-zag shape. The tear line 626 can extend from a portion of the recess 1622, such that a portion of the edge of the recess 1622 is weakened. The weakened portion can still include at least a portion of the first film, the second film, or both, such that the weakened portion does not form a slit or void of material.

In an example, the weakened portions of the tear line can be created by applying pressure, vibration, heat or other forces.

Figure 26:
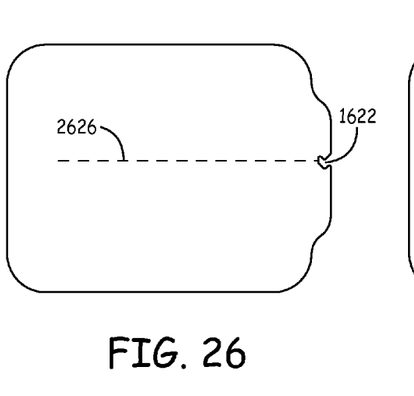
FIG. 26 is a front view of an envelope, according to an example.
Figure 27:
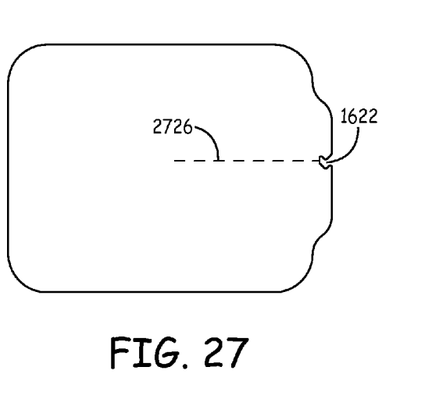
FIG. 27 is a front view of an envelope, according to an example.

In an example, the tear line 626 can terminate before reaching the opposite end of the envelope 100, such that a used envelope 100 ready to be discarded can be in one piece, as opposed to two pieces as shown in FIG. 21 and FIG. 22. FIG. 26 shows an example of a tear line 2626 that terminate before reaching the opposite edge of the envelope. The tear line 2626 can terminate before it reaches the seal area 102, such as terminating along the cavity 106. In an example, the tear line 2626 can terminate at the boundary of the cavity 106 and the seal area 102. FIG. 27 shows an example of a tear line 2726 that terminates before reaching the opposite edge of the envelope. The tear line 2726 can terminate along the cavity 106.

In an example, the first film can start off on a roll, such as a continuous roll of film. Similarly, the second film can be on a roll, such as a continuous roll of film. In an example the tear line can be added to the first film before the first film has been joined to the second film. The tear line can added in a way that is continuous along the first film in one example.

In an example where the first film of the barrier envelope also includes adhesive and a release liner, the adhesive and release liner can be applied to the first film when the first film is in a continuous form, before it is joined to the second film.

In an example, after the tear line has been added to the first film, the first film can be at least partially coupled to the second film, such as by heat sealing the first film with the second film, such as to define the seal area of a plurality of envelopes. After the first film is coupled to the second film, the envelopes can be separated using a cutting die. The envelopes can be separated from each other using many different methods and equipment, such as with a punch, with a laser, or by cutting. In an example, a cutting die used during the separation step can also create the notch and slot, while separating the individual envelope from the coupled films.

In an alternative example, the adhesive and release liner can be applied to the first film or second film and the tear line can be created on one of the films prior to coupling the first film with the second film. Then, the first film and the second film portions of envelopes can be separated from each other prior to coupling the first film with the second film. In an example, the first film can be coupled with the second film after the envelopes have been separated. In an example, the slit and notch can be punched or otherwise formed into the envelopes after the first film has been coupled to the second film.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred examples and techniques. However, it should be understood that many variations and modifications may be made while remaining within the spirit and scope of the invention.

The invention claimed is:

1. An envelope for an imaging plate, comprising:
a first film partially hermetically sealed with a second film in a sealed portion, the first film and second film defining a cavity between the first film and the second film, the cavity configured to receive an imaging plate;
an adhesive disposed on the first film or the second film along an unsealed portion of the first film and the second film;
a tab portion protruding from a remainder of the envelope; and
a recess defined by the first film and the second film within the tab portion and within the sealed portion;
wherein the first film or the second film define a slit that is separated from the recess by a portion of the first file or the second film.

2. The envelope of claim 1, wherein the sealed portion of the first film and the second film is around a portion of a periphery of the envelope.

3. The envelope of claim 1, wherein the recess is a Z-shaped recess.

4. The envelope of claim 1, wherein the recess is at least partially defined by a zig-zag side.

5. The envelope of claim 1, wherein the first film comprises an opaque film and the second film comprises a transparent film.

6. The envelope of claim 1, wherein an inner most portion of the recess is parallel with an edge of the envelope which the recess extends inwards from.

7. The envelope of claim 1, wherein the tab portion is centered between two sides of the envelope.

8. The envelope of claim 7, wherein the recess is centered in the tab portion.

9. An envelope for an imaging plate, comprising:
an first film partially hermetically sealed with a second film in a sealed portion, the first film and second film defining a cavity between the first film and the second film, the cavity configured to receive an imaging plate;
an adhesive disposed on the first film or the second film along an unsealed portion of the first film and the second film;
a recess defined by the first film and the second film within the sealed portion; and
a slit defined by the first film or the second film separated from the recess.

10. The envelope of claim 9, wherein the sealed portion is around a portion of a periphery of the envelope.

11. The envelope of claim 10, wherein the envelope has four sides, wherein the sealed portion is along three sides, and wherein the adhesive is present along a remaining side.

12. The envelope of claim 9, comprising a tab portion protruding from a remainder of the envelope.

13. The envelope of claim 9, wherein the slit extends through both the second and first films.

14. The envelope of claim 9, wherein the slit extends normal to the recess.

15. The envelope of claim 9, wherein the recess is at least partially defined by a zig-zag side.

16. The envelope of claim 9, comprising a tear line along one of the first film or the second film, wherein the tear line includes at least one weaker portion of the first film or the second film.

17. The envelope of claim 16, wherein the tear line extends from a portion of the recess in a direction to be approximately parallel to a top edge or bottom edge of the envelope.

18. The envelope of claim 16, wherein the tear line extends from a portion of the recess toward a side of the envelope that is opposite from the recess.

19. The envelope of claim 9, wherein an inner most portion of the recess is parallel with an edge of the envelop which the recess extends inwards from.

20. An envelope for an imaging plate, comprising:
an opaque film partially hermetically sealed with a transparent film in a sealed portion, the opaque film and transparent film defining a cavity between the opaque film and the transparent film, the cavity configured to receive an imaging plate;
an adhesive disposed on the opaque film or the transparent film along an unsealed portion of the opaque film and the transparent film;
a tab portion protruding from a remainder of the envelope, the tab portion being within the sealed portion;
a recess defined by the opaque film and the transparent film within the sealed portion and within the tab portion;
a tear line along one of the opaque film or the transparent film, wherein the tear line includes a series of weakened portions of the opaque film or the transparent film; and
a slit defined by at least one of the opaque film or the transparent film, and separated from the recess by at least a portion of the opaque film and the transparent film.

* * * * *